US008311847B2

(12) United States Patent
Kotula et al.

(10) Patent No.: US 8,311,847 B2
(45) Date of Patent: *Nov. 13, 2012

(54) DISPLAYING RADIOLOGICAL IMAGES

(75) Inventors: Jeffrey J. Kotula, Eden Prairie, MN (US); Wade J. Steigauf, Bloomington, MN (US); Tom J. Gleeson, Madison, WI (US); Sarah Osmundson, St. Louis Park, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 220 days.

This patent is subject to a terminal disclaimer.

(21) Appl. No.: 12/722,407

(22) Filed: Mar. 11, 2010

(65) Prior Publication Data

US 2011/0222746 A1  Sep. 15, 2011

(51) Int. Cl.
*G06Q 50/00* (2012.01)
*G06K 9/00* (2006.01)

(52) U.S. Cl. .............................. 705/2; 382/128; 382/305

(58) Field of Classification Search .................. 705/2–3
See application file for complete search history.

(56) References Cited

U.S. PATENT DOCUMENTS

| 6,891,920 | B1 | 5/2005 | Minyard et al. |
| 6,909,795 | B2 | 6/2005 | Tecotzky et al. |
| 7,212,661 | B2 | 5/2007 | Samara et al. |
| 7,525,554 | B2 | 4/2009 | Morita et al. |
| 7,756,725 | B2 | 7/2010 | DeJarnette et al. |
| 8,150,708 | B2 | 4/2012 | Kotula et al. |
| 2003/0179917 | A1 | 9/2003 | Faber et al. |
| 2003/0228042 | A1* | 12/2003 | Sinha ............................ 382/131 |
| 2006/0239395 | A1 | 10/2006 | Abe et al. |
| 2007/0019853 | A1 | 1/2007 | Luo |
| 2007/0118540 | A1 | 5/2007 | Guo |
| 2007/0197909 | A1 | 8/2007 | Kariathungal et al. |
| 2008/0117230 | A1 | 5/2008 | Wegenkittl et al. |
| 2008/0124002 | A1 | 5/2008 | Eichhorn |
| 2008/0240524 | A1 | 10/2008 | Kariathungal et al. |
| 2009/0103789 | A1 | 4/2009 | Danner et al. |
| 2010/0128946 | A1* | 5/2010 | Fidrich et al. ................. 382/131 |
| 2010/0211409 | A1 | 8/2010 | Kotula et al. |

FOREIGN PATENT DOCUMENTS

WO  WO-2010096438 A3  8/2010

OTHER PUBLICATIONS

"U.S. Appl. No. 12/372,593, Non Final Office Action mailed Mar. 17, 2011", 32 pgs.
"U.S. Appl. No. 12/372,503, Response filed Jun. 10, 2011 to Non final Office Action mailed Mar. 7, 2011", 14 pgs.
"U.S. Appl. No. 12/372,593, Examiner Interview Summary mailed May 27, 2011", 3 pgs.

(Continued)

*Primary Examiner* — Lena Najarian
*Assistant Examiner* — Minnah Seoh
(74) *Attorney, Agent, or Firm* — Schwegman Lundberg & Woessner P.A.

(57) ABSTRACT

The subject matter of this specification can be implemented in, among other things, a system for interfacing with multiple medical imaging modalities that includes a normalization module for normalizing hanging protocols for displaying medical images. The normalization can be executed as a function of similar image characteristics shared between multiple sequences of medical images.

19 Claims, 7 Drawing Sheets

OTHER PUBLICATIONS

"U.S. Appl. No. 12/372,593, Final Office Action mailed Jul. 14, 2011", 38 pgs.
"U.S. Appl. No. PCT/US2010/024415, International Search Report mailed Aug. 23, 2010", 3 pgs.
"International Application Serial No. PCT/2010/024415, Written Opinion mailed Aug. 23, 2010", 11 pgs.
"U.S. Appl. No. 12/372,593 , Response filed Nov. 11, 2011 to Final Office Action mailed Jul. 14, 2011", 15 pgs.
"U.S. Appl. No. 12/372,593, Examiner-Initiated Interview Summary dated Nov. 30, 2011", 1 pg.
"U.S. Appl. No. 12/372,593, Examiners Interview Summary mailed Nov. 8, 2011", 3 pgs.
"U.S. Appl. No. 12/372,593, Notice of Allowance mailed Jan. 25, 2012", 16 pgs.
"European Application Serial No. 10744223.8, Extended Search Report mailed May 9, 2012", 8 pgs.
"International Application Serial No. PCT/US2010/024415, International Preliminary Report on Patentability mailed Sep. 1, 2011", 10 pgs.
"Oracle Database New Features Guide 11g Release 1 (11.1)", [Online]. Retrieved from the Internet: <http://www.filibeto.org/sun/lib/nonsun/oracle/11.1.0.6.0/B28359_01/server.111/b28279.pdf >, (Accessed Apr. 24, 2012), 125 pgs.

* cited by examiner

DISPLAYING RADIOLOGICAL IMAGES

TECHNICAL FIELD

This document relates to displaying radiological images.

BACKGROUND

Medical images, such as X-rays, CAT (computerized axial tomography) scans, and MRIs (Magnetic Resonance Imaging), may be digitized to facilitate remote reading by radiologists. A hospital or other medical facility may use machines that capture and digitize the images and transmit them to a remote image server, such as a Picture Archiving and Communications System (PACS). The transmission may occur over a network, such as an intranet or the Internet.

Additionally, the hospital may also transmit orders corresponding to the images to an order server, such as a Radiologist Information System (RIS). The orders may be requests for a radiologist to interpret, or read, the images and return a diagnostic report. Orders may also contain information, such as a patient identifier, the procedure type associated with the image, patient demographic information, and a hospital identifier.

Radiologists can interpret medical images at a radiologist workstation. An image viewer application at the workstation receives the medical images and presents the medical images to the radiologist. The radiologist reviews the medical images and provides a report based on an analysis of the medical images. For example, the radiologist may provide a diagnosis of a particular medical condition, such as a tumor, based on the medical images.

SUMMARY

A system for generating a normalized hanging protocol using files, metadata, and medical images generated by multiple sources may include a normalization module that analyzes and normalizes the medical images. The files and metadata may be used to realize a normalized hanging protocol for displaying medical images generated by the multiple sources.

In an illustrative implementation, multiple medical facilities may generate sequences of medical images that have embedded metadata which specifies the modality that generated the images, a default grouping of the images, and a default ordering of the images within the groups, wherein the default ordering and grouping may be specific to particular types of modalities or facilities. In some embodiments, the various medical images and metadata may be received at an image order management system that parses the metadata and assembles the metadata into manifest files that may be transmitted independently to remote viewing sites, which in turn may be equipped with image viewer applications that analyze the manifest files and determine a normalized hanging protocol of the medical images. The normalized hanging protocol can represent a normalized order or layout of a series of arranged images for optimal electronic viewing. The normalization can be executed as a function of similar image characteristics shared between the multiple sequences of medical images.

In such implementations, the remote viewing site's image viewer application may call for the transmittal or caching of images for display in a status bar interface where the remote user can interact with the images displayed in a normalized hanging protocol.

The systems and techniques described here may provide one or more of the following advantages. First, providing normalized hanging protocols can allow radiologists to work in a unified environment that presents data from different facilities in a uniform way, regardless of the organization of the metadata in a corresponding manifest file. Second, providing normalized hanging protocols may enhance radiologist productivity since the radiologist can view all images in a standardized layout or fashion. Third, providing a status bar having a single click control can provide the advantage of quick retrieval of metrics during a dictation phase of a typical image study analysis. Fourth, providing an automatic scrolling mechanism may improve radiologist efficiency and reduce computer-related repetitive injuries.

The details of one or more embodiments are set forth in the accompanying drawings and the description below. Other features and advantages will be apparent from the description and drawings, and from the claims.

DETAILED DESCRIPTION

Illustrative implementations of computer-based systems, methods, and interfaces for generating, displaying, and adjusting radiological images are described. The described systems, methods, and interfaces can enable a radiologist in a teleradiology environment to view, interact with, and analyze images, and to provide diagnostic findings to a medical facility.

Figure 1A:
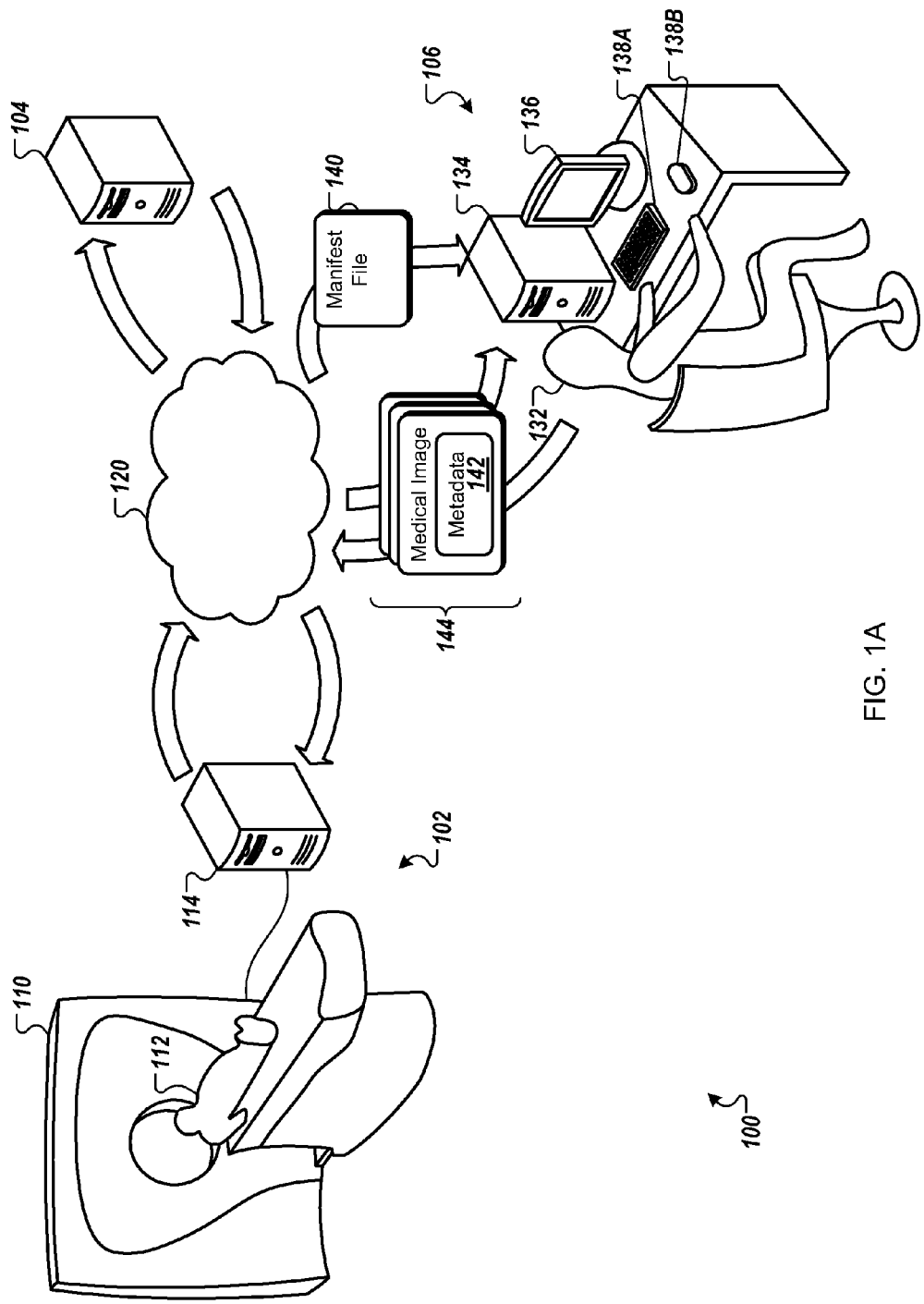
FIGS. 1A-B are diagrams showing examples of a teleradiology system.

Referring to FIG. 1A, an example teleradiology system 100 is shown. The system 100 can be used for capturing medical image data in one location and for reviewing medical images associated with the data in another location. The system 100 can include many geographically separated imaging devices and many image review terminals. For purposes of illustration, the teleradiology system 100 shown in FIG. 1 includes an imaging system 102, an image order (IO) management system 104, and an image review system 106. The imaging system 102, for example, may include an imaging device 110, such as a CT (computer tomography) scanner or an MRI (magnetic resonance imaging) scanner. Using an energy source such as X-rays or magnetic fields, for example, the imaging device 110 may capture image data associated with a subject 112 (e.g., a patient). In some implementations, the image data may include a series of two-dimensional images. In some implementations, the image data may be used to produce a three-dimensional model that can be further manipulated and reformatted for generating two-dimensional (or three-dimensional) images. Image data captured by the imaging device 110 can be stored and processed by an imaging device server 114 (e.g., one or more computers with a processor and a memory) and can be provided to other systems and computers in the system 100 through a network 120 (e.g. an intranet or the Internet).

In some implementations, image data may be provided to the IO management system 104, where the data may be stored and processed by one or more computers. For example, the IO management system 104 may determine that the image data is to be provided to a system user 132 (e.g., a radiologist) at the image review system 106. As shown, image data can be provided by the IO management system 104 to the image review system 106 through the network 120.

The image review system 106 may include an image display server 134 (e.g., one or more computers with a processor and a memory), a display device 136 (e.g., a monitor), and input devices 138A-B (e.g., keyboards, computer mice, joysticks, touch interfaces, voice interfaces, and the like). In some implementations, image data may be processed by the image display server 134 and visually presented to the user 132 as one or more images at the display device 136. Using the input devices 138A-B, the user 132 may interact with the presented images, for example, by manipulating one or more user controls included in a graphical user interface presented at the display device 136 in association with the images. For example, the user 132 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the user 132 may produce and indicate a diagnostic finding related to the subject 112.

In some implementations, the IO management system 104 generates one or more manifest files 140 that include a combination of medical images 144 and metadata 142 describing the medical images 144. The IO management system 104 may extract the metadata 142 from the medical images 144 and use the metadata 142 as a basis for modifying, reorganizing, or displaying information about the medical images 144. The IO management system 104 may generate one or more manifest files 140 that include the metadata 142 or additional metadata (not shown). The metadata 142 can be extracted from the medical images and compiled into the manifest file 140 that, for example, serves as a catalog, or manifest, of the medical images 144. The IO management system 104 can send the medical images 144 to a client device (e.g., image review system 106) independently of sending the manifest file 140 to the image review system 106. Similarly, the IO management system 104 can independently send the medical images 144 and the manifest file 140 to another client device (not shown). The image review system 106 (or another client device) may use the manifest file 140 to display, reorganize, analyze, or otherwise operate on medical images 144.

Each manifest file may include information about medical images arranged in a particular format. In an illustrative example, the manifest file may be generated using a Digital Imaging and Communications in Medicine (DICOM) format standard. The DICOM format includes metadata that describes the medical images. The manifest file 140 can, for example, describe an ordering and/or grouping in which to present the medical images 144. An image viewer application can receive the medical images 144 and present the medical images 144 in the ordering and/or grouping described in the manifest file 140.

In some implementations, the metadata 142 is embedded in a file that includes the medical images 144. For example, the metadata 142 may be included in header fields that accompany the medical image 144, where the header fields and the medical image 144 are transmitted together. In another example, an external requirement or regulation that applies to the medical image 144 may restrict separation of the metadata 142 from the medical image 144 (e.g., for compliance with the DICOM format standard).

Figure 1B:
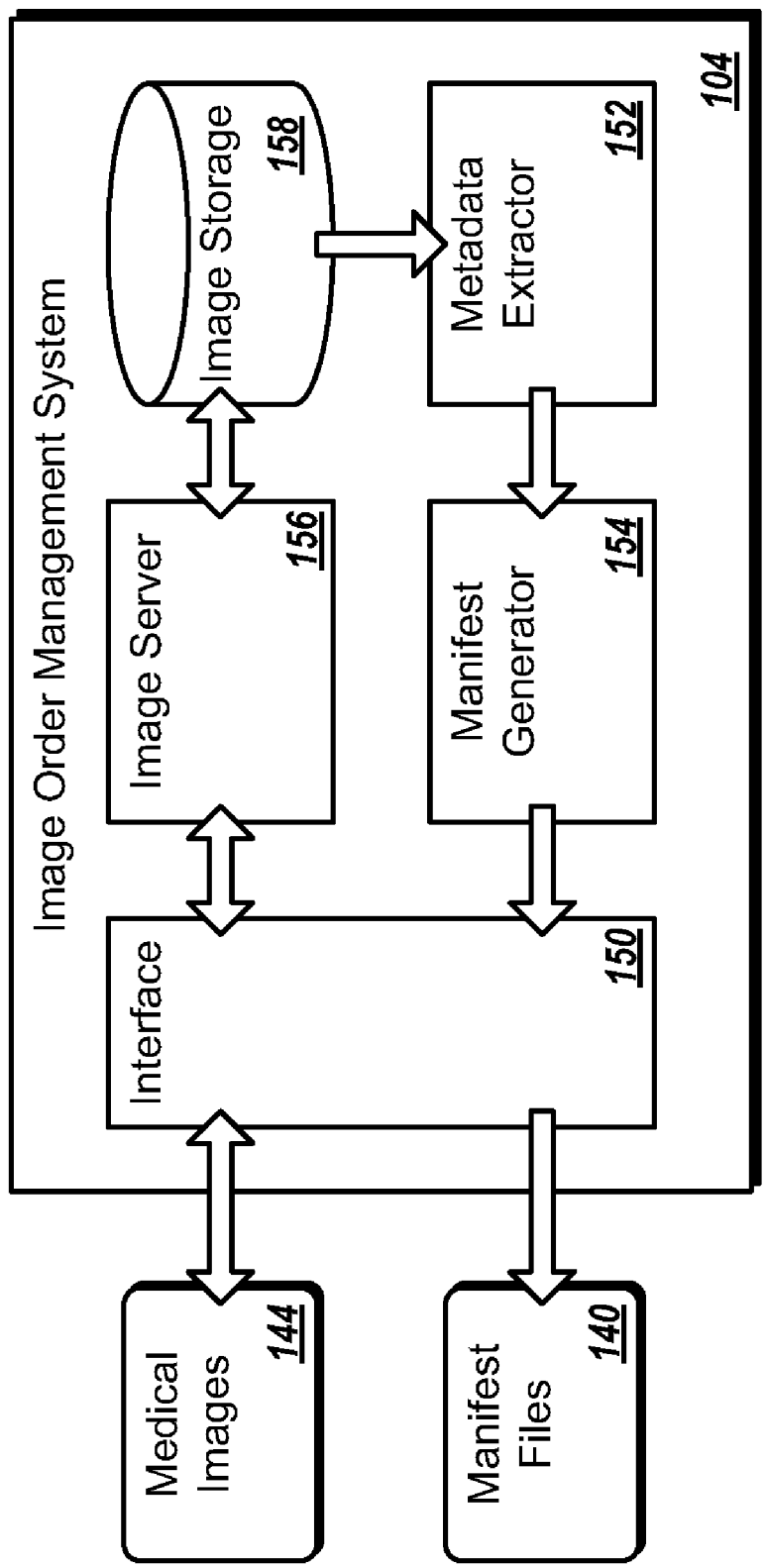

FIG. 1B is a block diagram showing an example of additional components in the IO management system 104. The IO management system 104 includes an interface 150, a metadata extractor 152, and a manifest generator 154.

The IO management system 104 uses the interface 150 to send and receive files or other data. For example, the IO management system 104 can receive the medical images 144 from a medical facility through the interface 150. In some implementations, the IO management system 104 can send the medical images 144 and corresponding manifest files 140 to an image server 156 through the interface 150. The image server can perform further processing on the medical images 144 and/or manifest files 140.

The image server 156 analyzes medical images including metadata associated with medical images. For example, the image server 156 can analyze metadata 142 stored in medical images 144. The metadata may be public metadata or private metadata. Public metadata may include information about the image data, such as the size, dimensions, bit depth, modality used to create the data, and equipment settings used to capture the image, among other information. Private metadata may include user-defined or vendor-defined metadata fields which provide additional information about the data or images. Both public and private metadata can be included in the DICOM file format and provided to the IO management system 104 in a manifest file 140, for example.

The metadata extractor 152 extracts metadata from medical images. For example, the metadata extractor 152 can receive the medical images 144 from the interface 150 and extract the metadata 142. The metadata extractor 152 provides extracted metadata to the manifest generator 154. In some implementations, the metadata extractor 152 stores the extracted metadata, for example, in image storage 158.

The manifest generator 154 uses extracted metadata to generate manifest files. For example, the manifest generator 154 can receive the metadata 142 from the metadata extractor 152 and generate the manifest files 140. The manifest generator 154 can use metadata or user-entered information to generate manifest files which specify instructions for presenting images in a specific manner. For example, the manifest generator 154 can generate a manifest file 140 which specifies using specific metadata (e.g., sub-specialty of a medical professional, user-specified data, or specific image capture device) for displaying an image sequence in a particular layout or order. In some implementations, the manifest generator 154 stores the generated manifest files, for example, in the image storage 158. The IO management system 104 provides one or more manifest files 140 to the image review system 106 through the interface 150.

While the example shown in FIGS. 1A-1B include a few medical images, the IO management system 104 can receive a number of medical images associated with a particular order that is significantly larger than a few images, such as hundreds or thousands of images. In addition, a medically relevant sequence of images can include any of the medical images received from a medical facility as determined by processing of the associated manifest file. Additionally, the medically relevant sequence may only include a portion of the medical images generated by a modality at a medical facility.

Figure 2:
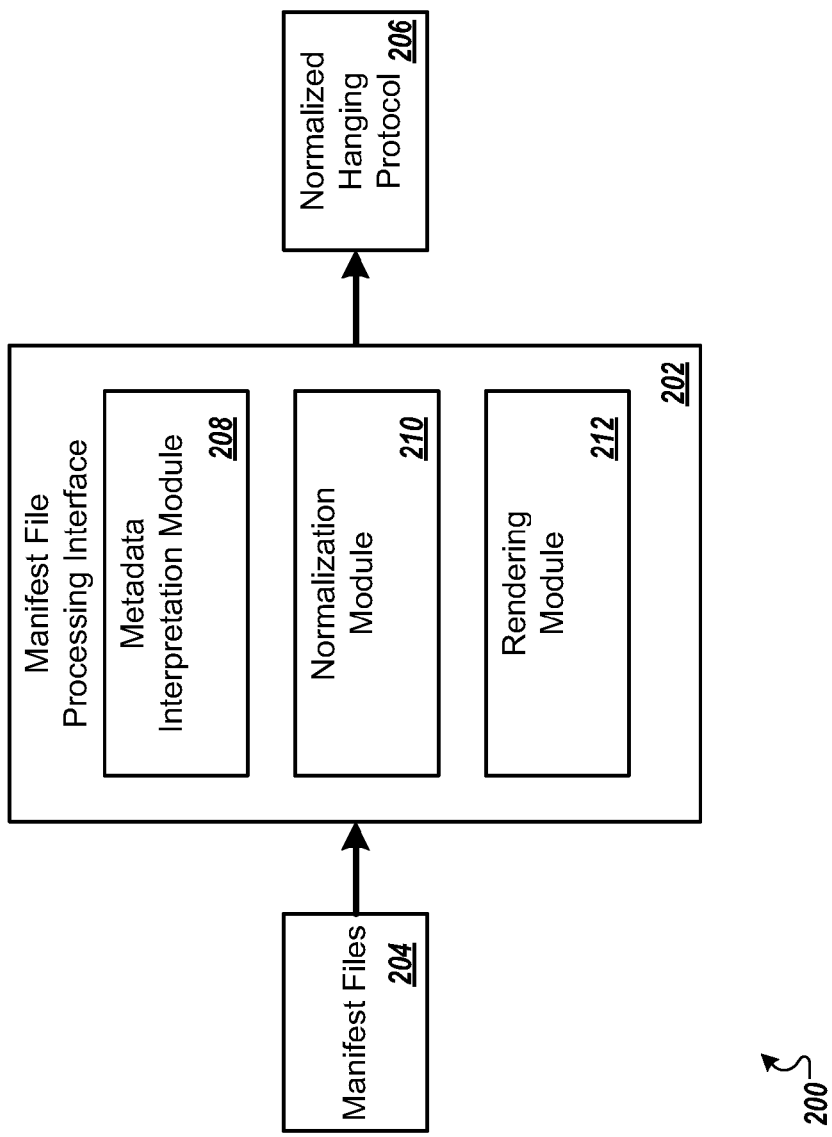
FIG. 2 is a block diagram of an example system for generating a normalized hanging protocol.

FIG. 2 is a block diagram of an example system for generating a normalized hanging protocol. A hanging protocol typically represents an order or layout of a series of arranged images for optimal electronic viewing. A normalized hanging protocol represents a hanging protocol capable of presenting specific types of images received from multiple different facilities in a consistent manner. The normalized hanging protocol may be normalized to similar image characteristic data included in metadata in one or more manifest files 202 received from a number of facilities, for example. Similar image characteristic data may include public or private metadata information or user-specified data included in manifest files received from multiple facilities.

Normalized hanging protocols can allow radiologists to work in a unified environment that presents data from different facilities in a uniform way, regardless of the organization of the metadata in a corresponding manifest file (e.g., DICOM format file). The normalization can ensure that radiologists can work with derived sequences of images that are organized according to image and study semantics rather than the vagaries of one or more sending devices or medical facility. Normalized hanging protocols may provide the advantage of enhancing radiologist productivity, for example because the radiologist can view all images in a standardized layout or fashion.

Referring to FIG. 2, the IO management system 104 (FIGS. 1A and 1B) may also include a manifest file processing interface 202. The manifest file processing interface 202 can receive transmissions from multiple medical facilities. The transmissions can include one or more manifest files which associate medical images and metadata describing characteristics of the medical images. The manifest file processing interface 202 can receive one or more manifest files 204 from the interface 150, for example.

The manifest file processing interface 202 can generate a normalized hanging protocol 206 by performing multiple processes on received manifest files 204. The processes can, for example, be performed by a metadata interpretation module 208, a normalization module 210, and a rendering module 212. Each module 208-210 can perform a number of processes simultaneously or concurrently with other processing tasks.

The normalization process performed in the manifest file processing interface 202 can include extracting and interpreting metadata from one or more manifest files 204. For example, the metadata interpretation module 208 extracts and interprets image characteristic data stored in the metadata of the manifest files 204. The interpretation may include generating a set of display rules for displaying the medical images received from each manifest file 204 according to a default hanging protocol. The default hanging protocol represents a set of standardized display rules received in metadata and employed by the IO management system 104. The display rules can include, for example, guidelines detailing the number of viewing panes in a GUI, an arrangement of viewing panes, and the content of the viewing panes as provided by each individual medical facility. In some implementations, the normalization process can include comparing image characteristics in two or more manifest files received from multiple facilities to create a normalized hanging protocol template for use in displaying images in several facilities.

The normalization module 210 can receive, from the metadata interpretation module 208, a default hanging protocol (e.g., display rules). The normalization module 210 modifies the default hanging protocol to display the medical images stored in each manifest file in a normalized fashion. The normalization may include normalizing the default hanging protocol to similar image characteristic data included in the metadata in one or more manifest files. In some implementations, a similarity standard or convention in the medical field, or particularly in the field of radiology, can be used as a similarity criterion. Solely as illustration herein, the image characteristic data may include: a modality that generated the images, a default grouping of the images, a default ordering of the images within the groups, a patient name, a patient identifier, a patient birth date, medical technician comments, a sub-specialty of a medical professional, user-entered preferences, a time the particular image was taken, a position of the image relative to the patient, a DICOM series number ("series #") that the image was originally included in, and the order of the image ("index") in the DICOM series, to name a few examples. Other image characteristic data is possible.

In some implementations, specific metadata in the default hanging protocol is omitted as part of the normalization process, which can provide a least common denominator representation of image characteristic data across multiple manifest files 204. This normalization reduces the amount of metadata required to provide a particular hanging protocol to a radiologist. In some implementations, the normalized hanging protocol can provide radiologists with hanging protocols corresponding to a sub-specialty of a medical professional, based on user-specified data, or corresponding to a specific image capture device, just to name a few examples. The normalization module 210 can use the normalized hanging protocol to create a standardized document manifest to determine which hanging protocol to employ.

The manifest file processing interface 202 can employ the rendering module 212 to prepare and display medical images from each manifest file 204. The rendering module 212 can display particular medical images in a status bar interface at a client device according to the normalized hanging protocol. The status bar interface can be used to display thumbnail images that can be selected by a radiologist for review in a larger display. The status bar can include images as well as controls for manipulating images in the larger display.

Figure 3:
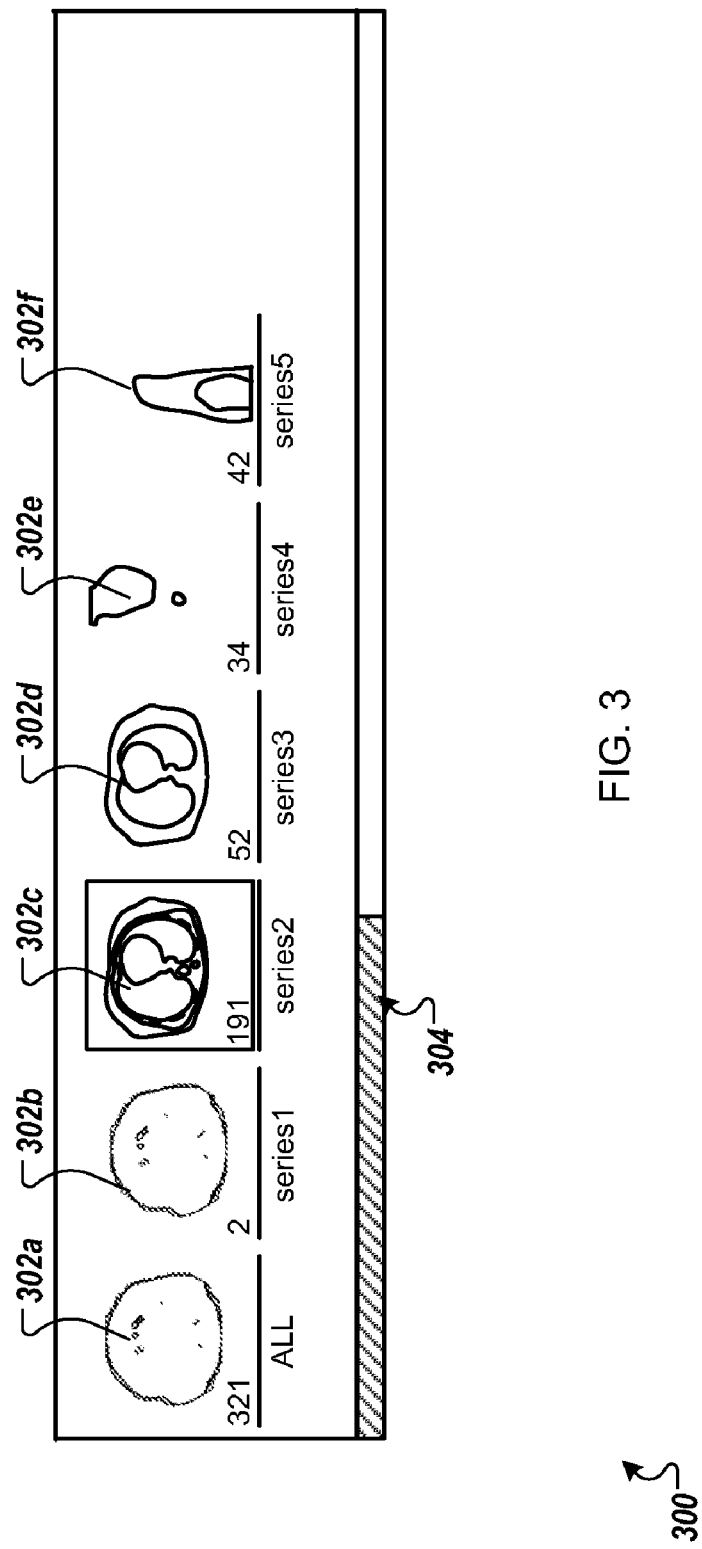
FIG. 3 is an illustration of an example status bar interface.

FIG. 3 is an illustration of an example status bar interface 300. The status bar interface 300 provides thumbnail images and user controls, and indicates a status of which images have been previously reviewed, modified, added, or deleted. In some implementations, the interface 300 may be displayed at the image display device 136 by the image review system 106 (as shown in FIG. 1). For example, the user 132 may use any of the input devices 138A-B to interact with one or more user controls included in the interface 300 to specify image adjustments (e.g., zooming, panning, rotating, contrast, color, view angle, view depth, rendering or reconstruction techniques). Based on the specified adjustments, for example, the teleradiology system 100 may generate one or more adjusted radiological images based on information received from the controls, and may present the adjusted image(s) at the image display device 136.

The status bar interface 300 depicts an interactive graphical user interface (GUI) for presenting, reviewing, and manipulating medical images organized according to a particular hanging protocol. The status bar interface 300 provides a number of image sequences here represented by respective thumbnails 302a-f. The thumbnail 302a represents an "all" sequence with a count of 321 images in the sequence. The thumbnails 302b-f represent "series #1" through "series #5," respectively. In some implementations, a sequence can be displayed according to a default hanging protocol. The default hanging protocol may display images in multiple panes according to each manifest file accompanying each image series. In some implementations, a sequence can be displayed according to a normalized hanging protocol. Each received image series can be analyzed by the IO management system 104 to determine similar image characteristics between the series. A similar image characteristic may involve image characteristics that are common to two distinct images. The commonality may be found in image metadata, image attributes, or other associated image data stored with each image file. The similar image characteristic can be deduced by comparing image data found in a manifest file associated with each image or image sequence, for example. The similar image characteristics can be used to organize and present images according to the normalized hanging protocol in a corresponding GUI (not shown).

The status bar interface 300 includes a status indicator 304 that indicates a review status for previously viewed images and a cache status of medical images in a study. For example, the status indicator 304 illustrates a placeholder in a sequence of images where a radiologist can continue reviewing images which have yet to be reviewed. A radiologist can use the status bar interface 300 for quickly ascertaining whether specific images or series of images have been reviewed. If the radiologist determines that one or more images or series have not been reviewed, the radiologist can jump to the unviewed images with a single-click control located on the status bar interface 300. For example, while a radiologist is viewing an image sequence, a single click in the sequence may cause the status bar interface 300 to jump to the next unviewed image within the current image sequence and display the next unviewed image in a larger display screen. If the radiologist decides to close out a study, the status bar interface 300 may generate a warning message that warns the radiologist of unviewed images and/or unviewed image series.

In some implementations, the status bar interface 300 can be used to review measurements, annotations, and/or key images that a radiologist has marked during the course of a read via a single click or selection of a button. Each reviewable metric can be displayed in a tiled mode on each available screen with the same imaging settings that were in effect when the metric was created or edited. Providing a single click control on the status bar interface 300 can allow quick retrieval of metrics during a dictation phase of a typical study read.

In some implementations, the status bar interface 300 may support an automatic scrolling mechanism. The scrolling mechanism can be triggered using an integrated ergonomic device, such as VRGrip, a standard mouse, joystick, or other scrolling capable hardware. The scrolling mechanism can facilitate image review by successively flipping through a series of images thus creating a motion picture, or automatic cine, of a particular patient's image series. The scrolling mechanism can be triggered with a single movement forward (using scrolling hardware) that sets an acceleration speed and immediately begins scrolling forward through an image sequence at the set acceleration speed. Similarly, the scrolling mechanism can be triggered by a single mouse movement sideways or backward to begin scrolling sideways or backward, respectively. If the scrolling is moving in a forward direction, the user can slow the scrolling speed by moving the scrolling hardware in a backward direction.

In general, scrolling speed can be increased and decreased depending on the amount of cursor movement, relative to the cursor's position at the time a cine is invoked by a user. For example, the user can use an input device, such as a mouse, in the same manner one would use a throttle mechanism. That is, the farther the user moves a mouse, the faster the cine scrolls. Similarly, the less the user moves the mouse, the slower the cine scrolls. The automatic scrolling mechanism may provide the advantages of optimizing radiologist efficiency and minimizing computer-related repetitive injuries since a constant scroll movement by the user is no longer required when employing the automatic scrolling mechanism.

Figure 4:
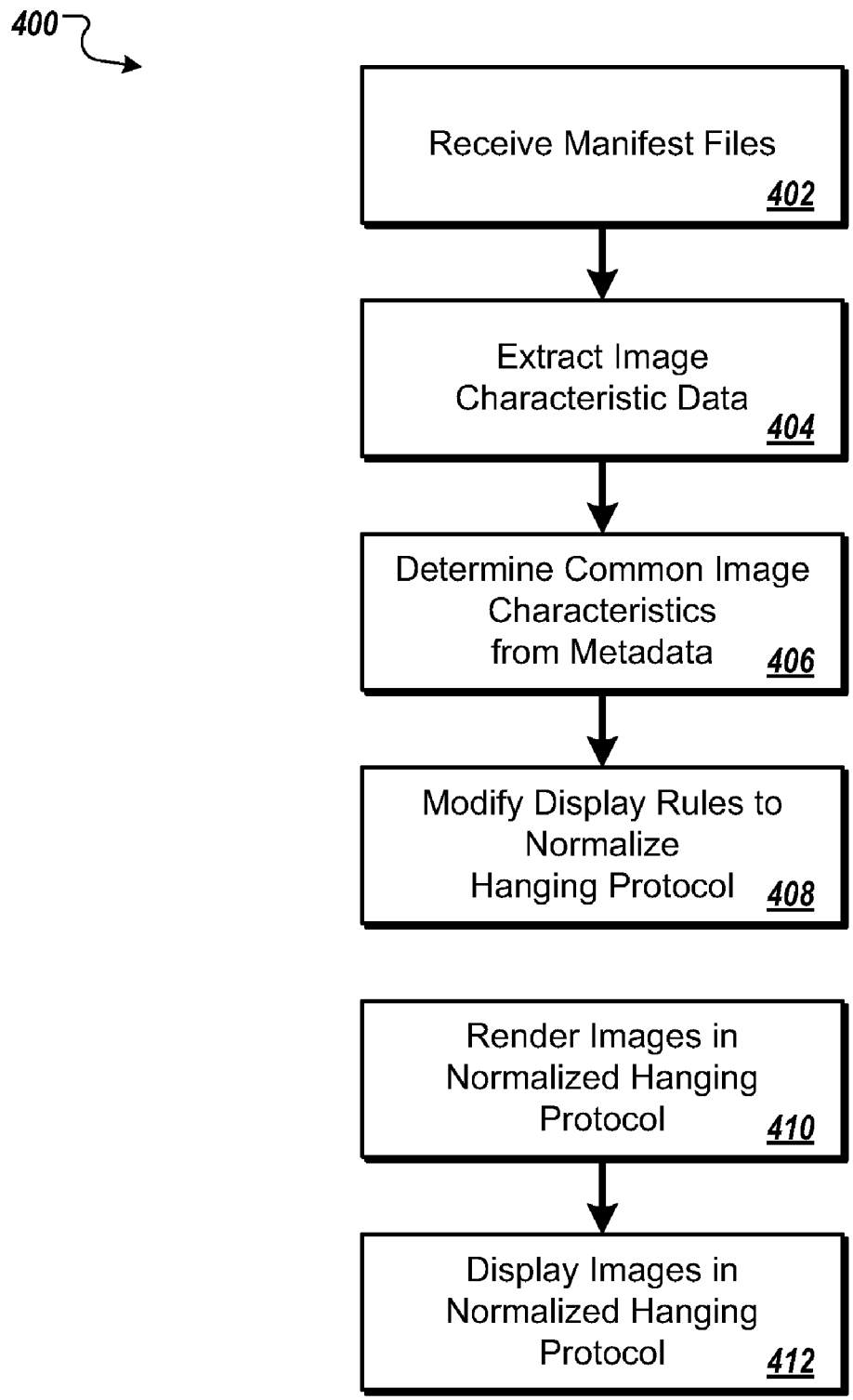
FIG. 4 is a flow chart showing an example process for normalizing a display protocol in a Picture Archiving and Communications System (PACS).

FIG. 4 is a flow chart showing an example process 400 for normalizing a display protocol in a Picture Archiving and Communications System (PACS). In some implementations, the process 400 may be performed by the system 200 (as shown in FIG. 2). In some implementations, the process 400 may be performed by the system 100 (as shown in FIG. 1). A particular order and number of steps are described for the process 400. However, it will be appreciated that the number, order, and type of steps required for the process 400 may be different in other examples.

In step 402, an image order management system (e.g., image order management system 104) receives one or more manifest files from medical facilities. The manifest files may include medical images and associated metadata describing characteristics of the medical images.

In step 404, a metadata interpretation module may extract the image characteristic data stored in the metadata of the manifest files and interpret the metadata. The metadata interpretation module can use interpreted metadata to generate display rules for displaying the medical images in each manifest file according to a first default hanging protocol.

In step 406, the metadata interpretation module may determine similar image characteristics included in the metadata in one or more manifest files. The similar image characteristics may in some implementations include user preferences, medical specialty, image semantics, and/or study semantics. For example, similar image characteristics of user preferences can include physician image layout preferences, radiologist image layout preferences, facility image layout preferences, and/or preferred header information. For example, similar image characteristics of medical specialties can include specialties such as oncology or neurology or a subspecialty such as radiation oncology or neuroradiology. For example, similar image characteristics of image semantics can include definitions or specific details about an image, including, but not limited to, physicians notes, patient requests, etc. For example, similar image characteristics of study semantics can include definitions or specific details regarding each image in an image study, including, but not limited to, file names, series name, patient history.

In step 408, a normalization module (e.g., normalization module 210) may modify the display rules to normalize the default hanging protocol into a normalized hanging protocol according to the determined similar image characteristics.

In step 410, a rendering module (e.g., rendering module 212) may render the medical images in at least the normalized hanging protocol. In step 412, the rendering module 212 may present the medical images in the normalized hanging protocol in a status bar display on a client device.

Figure 5:
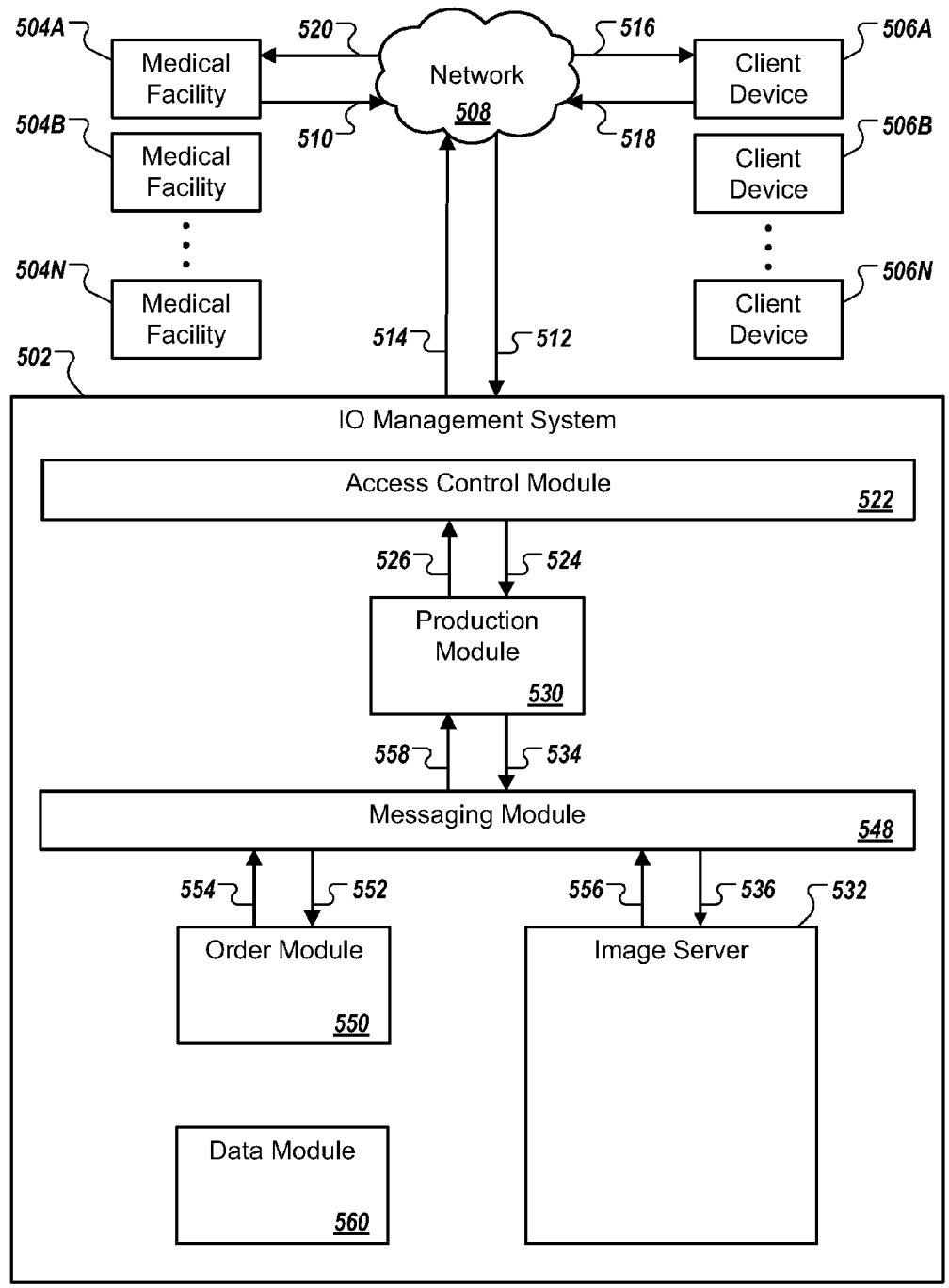
FIG. 5 is an example block diagram of a teleradiology system.

FIG. 5 shows an example block diagram of a teleradiology system 500 including an image order management system 502, medical facilities 504, and client devices 506 connected by a network 508, such as the Internet. The medical facilities 504 may send images and orders for studying the images to the IO management system 502, as represented by arrows 510 and 512. The images may include representations of body parts such as X-rays, CAT scans, and MRIs. The images may also contain information, such as which medical facility sent the image, the number of images in the transmission, the patient name, and other patient demographic information. The orders may contain information about a patient, such as name, medical history, and the reason the image was taken. The order may also include a description of an associated image, such as a pelvic abdominal scan, a number of images associated with the order, and an order type, such as preliminary or final read. The presence of the patient name and other patient information may enable a particular image to be linked with a particular order. The IO management system 502 may store the images and orders and assign the orders to appropriate users at the client devices 506. For example, the IO management system 502 may assign an order from a medical facility 504A to a radiologist at a client device 506A. If the radiologist accepts the order, the IO management system 502 may make the images associated with the order available to the radiologist for viewing, as indicated by arrows 514 and 516. The radiologist can interpret the images and send a report back to the IO management system 502, as represented by arrows 518 and 512. The IO management system 502 may then forward the report to the originating medical facility, as indicated by arrows 514 and 520, where the report may be used in a diagnosis for the patient.

The IO management system 502 may be implemented on a single computing device or on multiple computing devices, such as a server farm. In some implementations, the IO management system 502 may be disbursed over several servers that are connected through a network. This configuration may enable expansion of the system and flexibility in managing the flow of received and output images and orders.

Medical facilities may send images and orders at the same time as one another or at different times. Images, orders, and reports may be sent over the same network or different networks. For example, the IO management system 502 may receive images and orders through a single T1 connection to the Internet, or the images may be received from the Internet through a T1 connection and the orders may be received through a modem connection. As another example, the IO management system 502 may receive an image and an order from a medical facility over the Internet and return a corresponding report to the medical facility over a fax connection.

The images and orders may be sent separately or combined in one transmission. For instance, a computing device at a medical facility may use software that sends the orders and the images with a single application and single set of actions, or the medical facility may send the images using one application that sends one transmission and send the orders using a different application that sends a separate transmission.

In some implementations, the network 508 may be a secure network, such as a virtual private network (VPN). The VPN may include a secure computing device or terminal at the medical facility 504, at the IO management system 502, and at the client device 506. Encrypted transmissions (e.g., of image and order data) sent through the network 508 between the medical facility 504, the IO management system 502, and the client device 506 may also include the use of other forms of secure communications, such as the Secure Socket Layer (SSL), Terminal Services, and Citrix systems.

The IO management system 502 can include an access control module 522 that controls user access to the IO management system 502. Users may include staff at a hospital, imaging center, medical research facility or other medical facility and radiologists at the client devices 506, to name a few examples. For example, the access module 522 may include a remote desktop application, such as Terminal Services, that allows users to login to the IO management system 502. As another example, the access control module 522 may include an application portal accessible from the remote desktop or from the Internet with individual logins and passwords for each user. If the access control module 522 grants access to a user at the medical facility 504A, the user may be able to send images and orders or receive reports, as indicated by arrows 524 and 526, respectively. If an order is assigned to and accepted by a radiologist at the client device 506A, the radiologist may be able to retrieve the order and its images or send a report. The access control module 522 may also monitor the connectivity status of the medical facilities 504 or the client devices 506. For example, control module 522 may monitor whether a secure network connection between the medical facilities 504 or the client devices 506 and the I/O management system 502 is operational.

When image data is received by the IO management system 502 and accepted by the access control module 522 it may be sent to a production module 530. The production module 530 may handle real-time processing in the IO management system 502, such as managing the workflow of orders and images. The production module 530 may forward the image data to an image server 532, as indicated by arrows 534 and 536, for processing and storage. For example, the image server 532 may be part of a Picture Archive Communication System (PACS), which may digitally store, process, transmit, and facilitate the display of radiology images.

In some implementations, the production module 530 and the image server 532 may not communicate in the same format, so a messaging module 548 may handle communications between the two. For example, if the production module 530 is able to read text files as input, the messaging module 548 may take output from another source, such as the image server 532, and convert it into a text file format that the production module 530 can interpret.

When an order is received by the IO management system 502 and accepted by the access control module 522 it may be sent to the production module 530. The production module 530 may forward the order to an order module 550, such as a Radiology Information System (RIS), as represented by arrows 534 and 552, for processing. The messaging module 548 may process communication between the production module 530 and the order module 550.

Once the IO management system 502 receives an order, the production module 530 may assign the order to a user of a client device 506. The production module 530 may also assign the order to several users at several client devices 506. If the access control module 522 grants a user of a client device access, the user may retrieve orders from the order module 550 and image data from the image server 532, as indicated by arrows 554, 556, and 558.

The IO management system 502 may include a data module 560 that stores data associated with the system 502. For example, order data used by the order module 550 and image data used by the image server 532 may be stored by the data module 560. In some implementations, image data may be stored by the image server 532.

Figure 6:
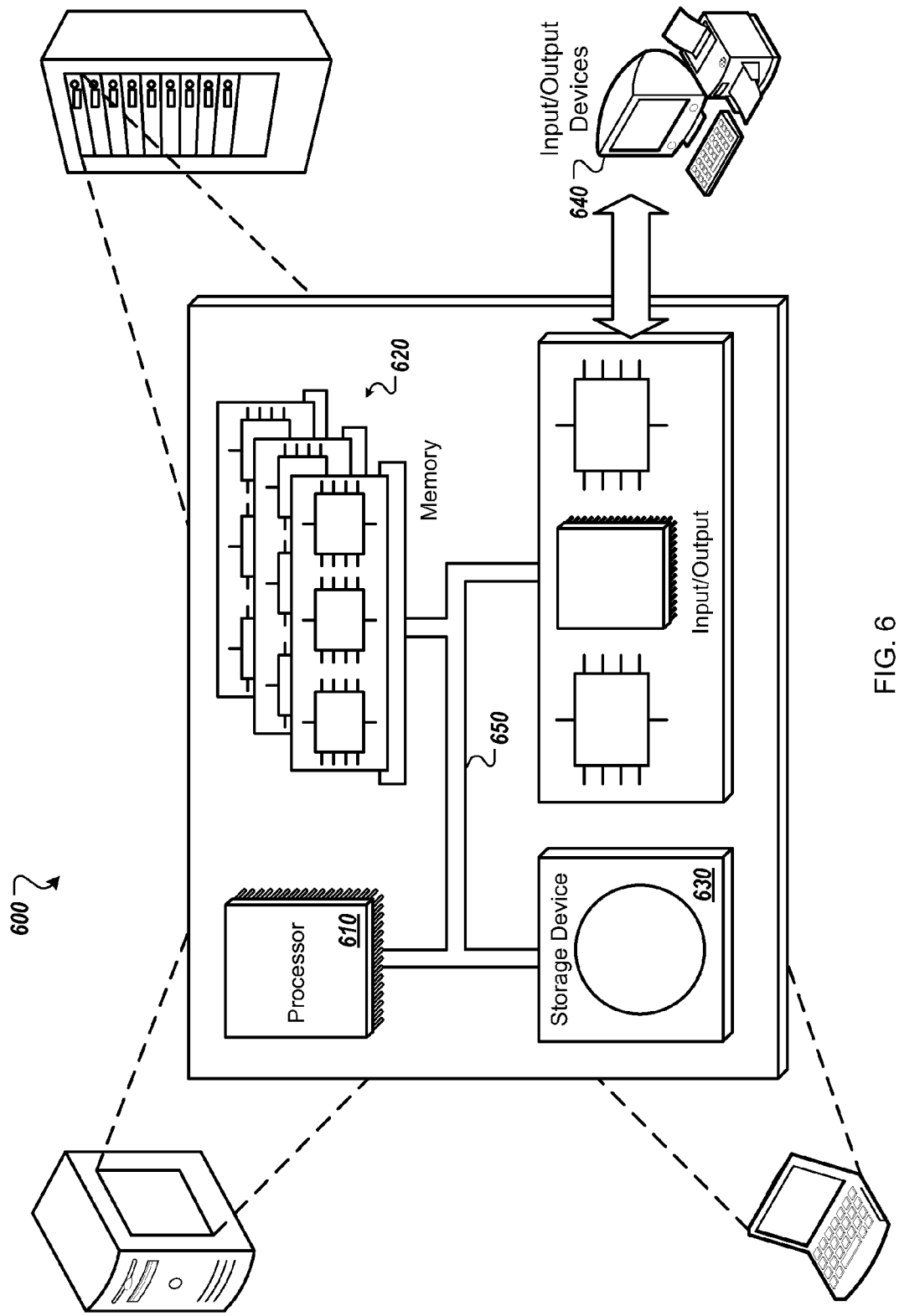
FIG. 6 is a block diagram of a generic computing system that can be used in connection with computer-implemented methods described in this document.

FIG. 6 is a schematic diagram of a generic computer system 600. The system 600 can be used for the operations described in association with any of the computer-implement methods described previously, according to some implementations. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. In some implementations, the processor 610 is a single-threaded processor. In some implementations, the processor 610 is a multi-threaded processor. The processor 610 is capable of processing instructions stored in the memory 620 or on the storage device 630 to display graphical information for a user interface on the input/output device 640.

The memory 620 stores information within the system 600. In some implementations, the memory 620 is a computer-readable medium. The memory 620 is a volatile memory unit in some implementations and is a non-volatile memory unit in other implementations.

The storage device 630 is capable of providing mass storage for the system 600. In some implementations, the storage device 630 is a computer-readable medium. In some implementations, the storage device 630 may be a floppy disk device, a hard disk device, an optical disk device, or a tape device.

The input/output device 640 provides input/output operations for the system 600. In some implementations, the input/output device 640 includes a keyboard and/or pointing device. In some implementations, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made without departing from the spirit and scope of this disclosure. Accordingly, other implementations are within the scope of the following claims.

What is claimed is:

1. A computer-implemented method for normalizing a display protocol in a picture archiving and communications system, the method comprising:
   receiving, by a computer system including at least one processor and at least one memory, a first transmission comprising one or more manifest files, the manifest files configured to associate medical images with image characteristic data, the image characteristic data being obtained from metadata of the medical images and describing characteristics of the medical images, and the manifest files being provided separately from the medical images and providing a catalog of the medical images;
   generating, by the computer system, a first protocol of display rules for displaying the medical images according to a first viewing layout, the display rules generated using the image characteristic data included in the manifest files, wherein the image characteristic data is used to generate a display of at least one imaging sequence of the medical images in an order or layout not defined by the metadata of the medical images;
   identifying, by the computer system, similar image characteristics included in the image characteristic data of one or more of the manifest files;
   modifying, by the computer system, the display rules to normalize the first protocol into a normalized protocol of display rules to provide a second viewing layout consistent with the identified similar image characteristics; and
   presenting, on a display device, the medical images with the second viewing layout according to at least the normalized protocol.

2. The method of claim 1, wherein the manifest files include at least two manifest files, wherein the at least two of the manifest files include user preferences, and the method further comprising determining at least one similar user preference indicated in the at least two of the manifest files, and using the similar user preference as a normalization factor for generating rules for the normalized protocol.

3. The method of claim 1, wherein the manifest files include information to indicate one or more medical specialties, and the method further comprising determining one or more similar medical specialties indicated in the manifest files, and in response to determining the similar medical specialties, using the similar medical specialties as a normalization factor for generating rules for the normalized protocol.

4. The method of claim 1, wherein the manifest files include information to indicate user preferences and medical specialties, and the method further comprising using a combination of similar user preferences and similar medical specialties indicated in the manifest files as a normalization factor for generating rules for the normalized protocol.

5. The method of claim 1, wherein the manifest files include information to indicate a sub-specialty of a medical professional, and the method further comprising determining similar image characteristics indicated in the manifest files, including determining the sub-specialty of a medical professional common to the manifest files.

6. A computer system, comprising:
at least one processor;
at least one memory; and
a plurality of modules configured for operation with the processor and the memory to provide normalizing of a display protocol for teleradiology, the plurality of modules including:
an interface module for receiving a first transmission comprising one or more manifest files that are separate from the medical images, the manifest files configured to associate the medical images with image characteristic data, the image characteristic data being obtained from metadata of the medical images and describing characteristics of the medical images;
a metadata interpretation module for generating a first protocol of display rules for displaying the medical images, the display rules generated using the image characteristic data obtained from the metadata according a first hanging protocol, wherein the image characteristic data is used to generate a display of at least one imaging sequence of the medical images in an order or layout not defined by the metadata of the medical images;
a normalization module for modifying the display rules to normalize the first protocol of display rules into a normalized protocol of display rules to provide a viewing layout consistent with the determined similar image characteristics; and
a rendering module for presenting, on a display device, the medical images according to at least the normalized protocol.

7. The computer system of claim 6, wherein the rendering module configures sequences of medical images for automatic scrolling in a picture archiving and communications system.

8. The computer system of claim 6, wherein the manifest files include at least two manifest files, wherein the at least two of the manifest files include user preferences, and wherein the normalization module determines at least one similar user preference indicated in the at least two of the manifest files, and uses the similar user preference as a normalization factor for generating rules for the normalized protocol.

9. The computer system of claim 6, wherein the manifest files include information to indicate one or more medical specialties, and wherein the normalization module determines one or more similar medical specialties indicated in the manifest files, and uses the similar medical specialty as a normalization factor for generating rules for the normalized protocol.

10. The computer system of claim 6, wherein the manifest files include information to indicate user preferences and medical specialties, and wherein the normalization module uses a combination of similar user preferences and similar medical specialties indicated in the manifest files as a normalization factor for generating rules for the normalized protocol.

11. The computer system of claim 6, wherein the manifest files include information to indicate a sub-specialty of a medical professional, and wherein the normalization module determines a sub-specialty of a medical professional common to the manifest files.

12. A non-transitory computer-readable data storage medium storing computer-executable instructions that, when executed, perform a method for normalizing a display protocol in a teleradiology system, the method comprising:
receiving a first transmission comprising one or more manifest files associating medical images with image characteristic data, the image characteristic data being obtained from metadata of the medical images and describing characteristics of the medical images;
generating a first protocol of display rules for displaying the medical images according to a first viewing layout, the display rules generated using the image characteristic data included in the manifest files, wherein the image characteristic data is used to generate a display of at least one imaging sequence of the medical images in an order or layout not defined by the metadata of the medical images;
identifying similar image characteristics included in the image characteristic data of one or more of the manifest files;
modifying the display rules to normalize the first protocol into a normalized protocol of display rules to provide a second viewing layout consistent with the identified similar image characteristics; and
presenting, on a display device, the medical images with the second viewing layout according to at least the normalized protocol.

13. The method of claim 1, wherein the normalized protocol includes a normalized hanging protocol to provide an consistent order of a series of arranged images for electronic viewing of the medical images.

14. The method of claim 1, wherein the manifest files include at least two manifest files received from respective medical facilities, and wherein modifying the display rules to normalize the first protocol into a normalized protocol results in providing the second viewing layout according to at least the normalized protocol for medical images from the respective medical facilities.

15. The computer system of claim 6, wherein the normalized protocol of display rules includes a normalized hanging protocol used to provide an consistent order of a series of arranged images for electronic viewing of the medical images.

16. The computer system of claim 6, wherein the manifest files include at least two manifest files received from respective medical facilities, and wherein modifying the display rules to normalize the first protocol of display rules into a normalized protocol of display rules results in providing the viewing layout according to at least the normalized protocol for medical images from the respective medical facilities.

17. The computer system of claim 6, wherein the manifest file is generated by a manifest generator using metadata produced from a metadata extractor, the metadata extractor configured to extract specific metadata from the medical images.

18. The computer-readable data storage medium of claim 12, wherein the normalized protocol is a normalized hanging protocol used to present a consistent order of the medical images on the display device.

19. The computer-readable data storage medium of claim 12, wherein the manifest files include at least two manifest files received from respective medical facilities, and wherein modifying the display rules to normalize the first protocol into a normalized protocol results in providing the viewing layout according to at least the normalized protocol for medical images from the respective medical facilities.

* * * * *